United States Patent [19]

Hoskins et al.

[11] Patent Number: 4,740,203
[45] Date of Patent: Apr. 26, 1988

[54] REFILLABLE INJECTION DEVICE

[75] Inventors: Matthew W. Hoskins; Albert K. Chin, both of Palo Alto, Calif.

[73] Assignee: Thomas J. Fogarty, Palo Alto, Calif.

[21] Appl. No.: 871,462

[22] Filed: Jun. 5, 1986

[51] Int. Cl.[4] .............................................. A61M 29/02
[52] U.S. Cl. .................... 604/191; 128/344; 604/207; 604/236; 604/271; 604/247; 604/248; 604/97
[58] Field of Search ................ 128/344; 604/191, 207, 604/218, 236, 247, 256, 97, 248, 271

[56] References Cited

U.S. PATENT DOCUMENTS

| 857,739 | 6/1907 | Kennerly et al. | 604/191 |
| 4,271,839 | 6/1981 | Fogarty et al. | 128/344 |
| 4,446,867 | 5/1984 | LeVeen et al. | 604/97 |
| 4,476,866 | 10/1984 | Chin | 128/344 |
| 4,560,378 | 12/1985 | Weiland | 604/256 |
| 4,610,666 | 9/1986 | Pizzino | 604/191 |

FOREIGN PATENT DOCUMENTS

| 0018540 | 7/1935 | Australia | 604/236 |
| 0419869 | 10/1925 | Fed. Rep. of Germany | 604/82 |

Primary Examiner—C. Fred Rosenbaum
Assistant Examiner—Gene B. Kartchner
Attorney, Agent, or Firm—Limbach, Limbach & Sutton

[57] ABSTRACT

In a refillable injection device for use with a dilation catheter, a large bore syringe is used to refill a small bore syringe without disconnecting the syringe assembly from the catheter. A one-way valve prevents fluid from moving in the opposite direction. Movement of the small bore syringe plunger produces a high pressure, low volume flow and can be repeated if necessary after the small bore syringe is refilled. Subsequent movement of the large bore syringe plunger produces a low pressure, high volume flow.

13 Claims, 1 Drawing Sheet

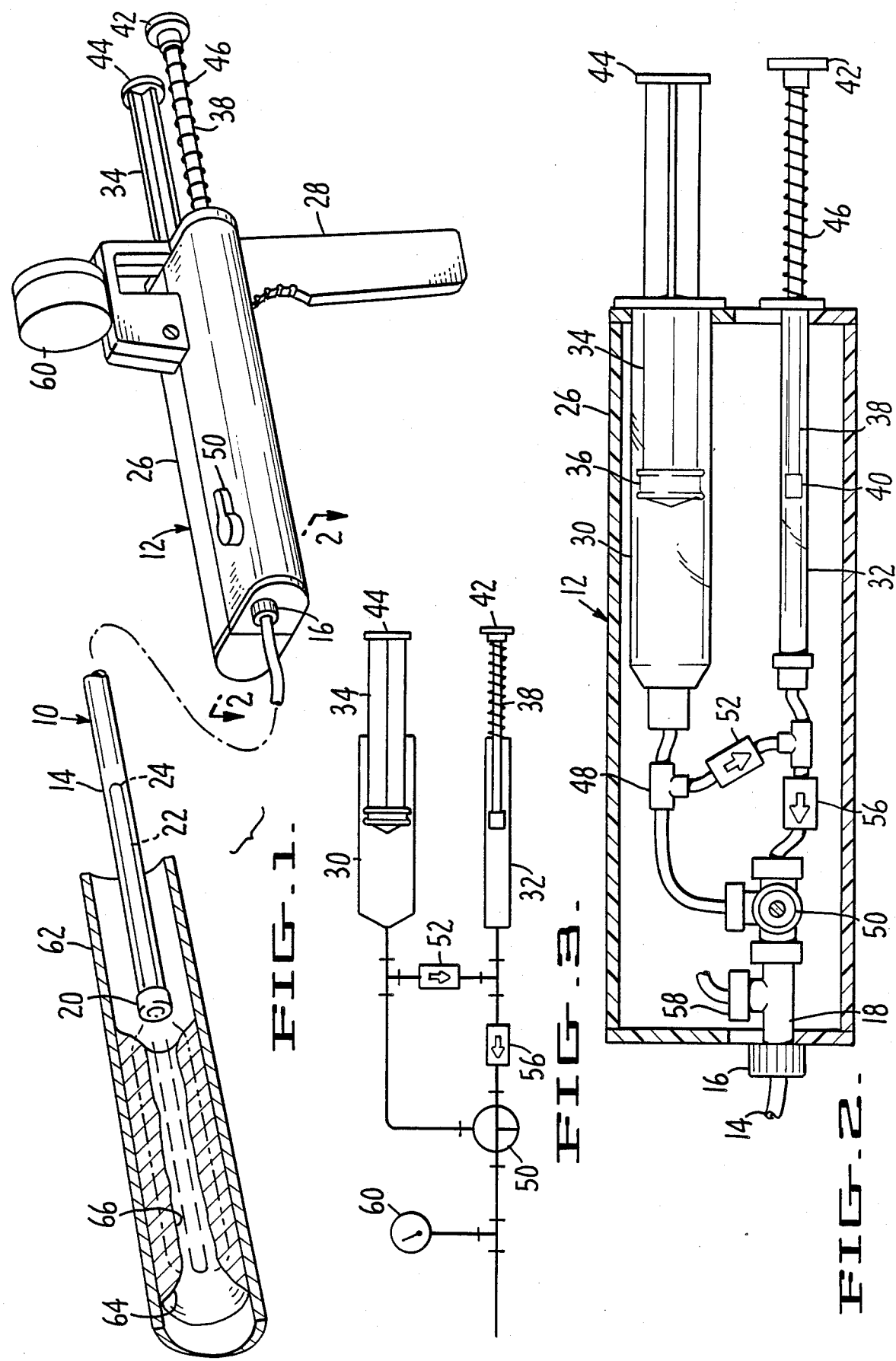

REFILLABLE INJECTION DEVICE

BACKGROUND OF THE INVENTION (1) Field of the Invention

The field of the invention is in the broad sense medical syringes. More specifically, the invention relates to dilatation catheters of the inversion-eversion type and an actuator therefor characterized by the use of a large bore syringe to refill a small bore syringe without having to disconnect the syringe assembly from the catheter during the eversion process.

(2) Description of the Prior Art

We are not aware of any device in which a large bore syringe is used to refill a small bore syringe during the process of everting a catheter balloon.

A method of inflating a catheter balloon by means of a Combined Large and Small Bore Syringe is shown by Chin, U.S. Pat. No. 4,476,866.

SUMMARY OF THE INVENTION

The gist of the invention is the provision in an invert-evert dilatation catheter of actuator means comprising large and small bore syringes, and a conduit means and check valve means connecting the syringes and allowing fluid to flow only from the large syringe to the small one so that it may be refilled during use without disconnecting it from the catheter.

The device may be used in situations such as those which prompted the design of the device of Chin, U.S. Pat. No. 4,476,866, the Combined Small and Large Bore Syringe. With the present device and the device of that patent, a first stage, a small bore syringe, is used to evert the balloon element under high pressure, low volume conditions and a second stage, a large bore syringe, can be used to inflate the balloon element under low pressure, high volume conditions. In the Combined Small and Large Bore Syringe, however, the small bore syringe cannot be refilled and thus high pressure can be developed over only the limited volume of the small bore syringe, typically 1 cc. In practice, 2 or 3 cc. of volume may be required at high pressure to initiate extrusion of the balloon, precluding use of the earlier design in such instances.

The current invention solves this problem by allowing the small bore syringe to be refilled from the large bore syringe without interfering with the operation of either or requiring that the device be disconnected from the catheter.

BRIEF DESCRIPTION OF THE DRAWINGS

FIG. 1 is a view in perspective of the syringe of the invention attached to a dilatation catheter disposed in treating relationship to an occluded blood vessel.

FIG. 2 is a sectional-elevational view of the syringe portion of the apparatus on the plane designated by line 2—2 in FIG. 1.

FIG. 3 is a schematic diagram of the flow circuit of the device shown in FIGS. 1 and 2.

DESCRIPTION OF THE PREFERRED EMBODIMENT

Referring to FIGS. 1 and 2, the device of the invention is comprised of a dilatation catheter portion indicated generally at 10 and a syringe portion indicated generally at 12. The catheter portion 10 is comprised of an elongated flexible tube 14 having its proximal end attached by fitting means 16 to the distal end 18 of syringe pdrtion 12. Sleeved over and fixedly attached to the distal end of tube 14 is the proximal end 20 of an elongated balloon element 22 having a closed distal end 24. The balloon element is made of non-elastomeric plastic material such as thin vinyl tubing.

The syringe portion 12 comprises a housing 26 mounted on a handle 28 and containing therein a large bore syringe 30 and a small bore syringe 32. Slidably disposed within the large bore, syringe 30 is a piston element comprising a flexible land 36 and rod 34 to which the land is fixedly attached, while a similar piston member comprising a flexible land 40 and rod 38 to which the land is fixedly attached is slidably disposed within the small bore syringe 32. The rods 38 and 34 are provided with a typical cruciform cross-section which terminates at the proximal ends in pusher discs 42 and 44, respectively. Surrounding the portion of rod 38 extending between the housing 12 and pusher disc 42 is a spring 46, which operates to keep the rod 38 extended as far as possible out of the small bore syringe 32 unless manual pressure is applied in the opposite direction. A stop prevents the piston 38 from being completely withdrawn from the syringe. The volume of the large bore syringe 30 is preferably a plurality of times as great as the volume of the small bore syringe 32.

The distal outlet end of the large bore syringe 30 is connected to a T-fitting 48, one outlet of which is connected to a three-way valve 50 and the other through one-way valve 52 to another T-fitting 54. One outlet of T-fitting 54 is connected to the distal outlet end of small bore syringe 32 and the other through one-way valve 56 to three-way valve 50. The arrows on one-way valves 52 and 54 show the direction of permitted fluid flow. The resulting fluid circuit allows fluid to flow from the large bore syringe 30 either to three-way valve 50 or into small bore syringe 32. Fluid from small bore syringe 32 may flow to three-way valve 50 but not back into large bore syringe 30. No fluid may flow directly from three-way valve 50 into small bore syringe 32.

Three-way valve 50 has three openings, one leading to T-fitting 48, one to one-way valve 56 (but the valve prevents fluid from flowing in that direction) and one to distal end 18 of the syringe portion 12. Three-way valve 50 may be operated to close off any one of these three passages, or to leave all three open at once. Fitting 58 is connected to pressure gauge 60 and allows use of the gauge to monitor the pressure in the catheter 14.

The catheter syringe is shown in condition for operation in FIG. 1. The catheter portion 10 is positioned within an artery 62 adjacent a section of arteriosclerotic material 64. The balloon element 22 is inverted within tube 14. The tube 14 is otherwise filled with a liquid which also fills large bore syringe 30, small bore syringe 32 and all the passageways interconnecting them with distal end 18 of syringe portion 12, including the valves 50, 52 and 56.

With three-way valve 50 open from one-way valve 56 to distal end 18, and the direction to T-fitting 48 closed, the user pushes on pusher disc 42, causing the rod 38 to move within small bore syringe 32 and causing a high pressure, low volume flow into catheter tube 14. Such flow imparts a high eversion force to the balloon element 22, very readily and easily causing the balloon element to evert and extend within the lumen 66 of arteriosclerotic material 62. Upon completion of the stroke, the rod 38 is returned to its original position by spring 46. The resulting suction draws fluid into small bore syringe 32 from large bore syringe 30 through T-fittings 48 and 54 and one-way valve 52, since no fluid can return through one way valve 56. If more volume is needed to fully evert the balloon element 22, this high pressure, low volume injection with the small bore syringe 32 can be repeated several times.

After the balloon is fully everted, three way valve 50 is operated to open a passageway from T-fitting 48 to distal end 18. (The passageway from one-way valve 56 to distal end 18 may be open or closed.) The user then pushes the pusher disc 44, causing the rod 34 to move within large bore syringe 30 and causing a low pressure, high volume flow of liquid into the tube 14 to radially expand the balloon element 22 and thereby dilate the arteriosclerotic material 64. Such low pressure, high volume flow may continue as long as desired, as long as the capacity of large bore syringe 30 is great enough.

After dilatation is complete, pusher disc 44 may be retracted; the resulting vacuum in large bore syringe 30 will cause water to flow into it from the tube 14, thus aspirating and deflating the balloon element 22. Finally, the large bore syringe 30 may be refilled through distal end 18 if the catheter is disconnected.

The invention has the further advantage that, since both syringes are controlled by manual application of pressure, the operator retains the feel and control of the inflation process.

CONCLUSION

From the foregoing description it is believed apparent that the present invention provides an improved syringe assembly for supplying both high pressure, low volume and low pressure, high volume fluid flows to evert and inflate a balloon catheter, without the necessity of disconnecting the catheter or manually refilling the small bore syringe which provides the high pressure, low volume flow where the volume of the small bore syringe alone is insufficient to fully evert the balloon. It should be understood, however, that the invention is not intended to be limited to the specific embodiments described, but rather is defined by the accompanying claims.

What is claimed:

1. A dual pressure syringe assembly comprising;
   a large bore syringe;
   a small bore syringe;
   conduit means interconnecting said syringes whereby said large bore syringe may discharge either into said small bore syringe or directly from the assembly; and
   check valve means in said conduit means to prevent back flow from said small bore syringe to said large bore syringe.

2. An assembly according to claim 1 wherein the volume of the large bore syringe is a plurality of times as great as the volume of the small bore syringe.

3. An assembly according to claim 1 further comprising manually operable valve means to selectively close the small bore syringe from discharge.

4. An assembly according to claim 3 wherein said manually operable valve means is also operable to open the large bore syringe to direct discharge independent of flow therefrom through the small bore syringe.

5. A dilatation catheter according to claim 1 wherein the small bore syringe has a plunger movable between charging and discharging positions and further comprising spring means to return the plunger to the charging position to automatically refill the small bore syringe from the large bore syringe.

6. In combination, a dilatation catheter comprising a catheter portion having proximal and distal ends and a syringe portion having a distal outlet end attached to the proximal end of the catheter portion, said catheter portion comprising an elongated flexible tube having an invertible-eversible balloon element attached to and received within the distal end thereof, and said syringe assembly portion comprising a large bore syringe, a small bore syringe, conduit means interconnecting said syringes whereby said large bore syringe may discharge into said small bore syringe, and check valve means in said conduit means to prevent reverse flow from said small bore syringe to said large bore syringe.

7. A dilatation catheter according to claim 6 wherein the volume of the large bore syringe is a plurality of times as great as the volume of the small bore syringe.

8. A dilatation catheter according to claim 6 further comprising manually operable valve means to selectively close the small bore syringe from discharge.

9. A dilatation catheter according to claim 8 wherein said manually operable valve means is also operable to open the large bore syringe to direct discharge independent of the flow therefrom through the small bore syringe.

10. A method of everting and inflating an invertible-eversible balloon element of a dilatation catheter from a position within the lumen of the catheter body comprising the following steps:
    disposing a fluid in the catheter body;
    injecting a low volume of fluid into the catheter body at high pressure by means of a small bore syringe such that the balloon is at least partially everted;
    upon exhaustion of the fluid in the small bore syringe, refilling the small bore syringe from a large bore syringe;
    repeating the injection of a low volume of fluid into the catheter body at high pressure by means of the small bore syringe and refilling the small bore syringe until the balloon is everted; and
    injecting a large volume of fluid into the catheter body at low pressure by means of the large bore syringe until the balloon is inflated.

11. A dual pressure syringe assembly having a common discharge port comprising a large bore cylinder with a large bore piston fitted therein, a small bore cylinder with a small bore piston fitted therein, said large bore cylinder having an outlet in communication with an outlet of the small bore cylinder through a first one-way valve and in communication with the discharge port of the assembly through a multiposition valve when said multiposition valve is in one position, the outlet of the small bore cylinder being in communication with the discharge port of the assembly through both a second one-way valve and the multiposition valve when the multiposition valve is in another position.

12. An assembly according to claim 11 wherein the small bore piston is movable between charging and discharging positions and further comprising spring means to return said small bore piston to the charging position to automatically refill the small bore syringe from the large bore syringe.

13. In combination, a dilatation catheter comprising a catheter portion having proximal and distal ends and a syringe portion having a distal outlet end attached to the proximal end of the cathter portion, said catheter portion comprising an elongated flexible tube having an invertible-eversible balloon element attached to and received within the distal end thereof, and said syringe assembly portion comprising a large bore syringe, a small bore syringe having a plunger movable between charging and discharging positions, conduit means interconnecting said syringes whereby said large bore syringe may discharge into said small bore syringe, check valve means in said conduit means to prevent reverse flow from said small bore syringe to said large bore syringe, and spring means to return said plunger to the charging position to automatically refill the small bore syringe from the large bore syringe.

* * * * *